United States Patent [19]

Bertolini et al.

[11] 4,289,654
[45] Sep. 15, 1981

[54] SUPPORTED CATALYST FOR THE OXIDATION OF ACROLEIN INTO ACRYLIC ACID

[75] Inventors: Natale Bertolini, Milan; Natale Ferlazzo, Segrate, both of Italy

[73] Assignee: Euteco Impianti S.p.A., Milan, Italy

[21] Appl. No.: 100,807

[22] Filed: Dec. 6, 1979

[30] Foreign Application Priority Data

Dec. 12, 1978 [IT] Italy .................................. 30718 A/78

[51] Int. Cl.³ .......................... B01J 23/20; B01J 23/24
[52] U.S. Cl. ................................ 252/456; 252/455 R; 252/458; 252/464; 252/465
[58] Field of Search ............... 252/454, 456, 458, 464, 252/465; 562/535

[56] References Cited

U.S. PATENT DOCUMENTS

| | | | |
|---|---|---|---|
| 3,525,101 | 8/1970 | Young et al. | 252/456 X |
| 3,775,474 | 11/1973 | Ohara et al. | 562/535 |
| 3,962,322 | 6/1976 | Richardson | 252/456 X |
| 4,014,925 | 3/1977 | Ferlazzo et al. | 562/535 |
| 4,035,262 | 7/1977 | Childress et al. | 252/456 |
| 4,170,572 | 10/1979 | Kurtz et al. | 252/456 X |

*Primary Examiner*—Carl F. Dees

*Attorney, Agent, or Firm*—Sughrue, Mion, Zinn, Macpeak & Seas

[57] ABSTRACT

Catalyst active in the oxidation of acrolein into acrylic acid, which comprises a silica or alumina support and from 15 to 80% by weight, with respect to the catalyst, of a catalytically active part having the following chemical composition $$Mo_aV_bW_cCu_dX_xO_y$$

wherein X is Cr, Mn, Fe, Co, Ni, Zn, Cd, Al or Sb and wherein for $a=12$, b ranges from 4 to 8, c ranges from 1 to 4, d ranges from 2 to 5, x ranges from 0 to 1 and y ranges from about 17 to about 72; said active part having an amorphous and bidimensional structure with an interplanar distance of 3.98 Å and an IR spectrum with a broad band at 860 cm$^{-1}$. The catalyst is obtained by impregnation of the support with an aqueous solution of decomposable salts of the metals of said active part, drying and activation in an oxidizing atmosphere and then in an inert atmosphere, the cycle of impregnation, drying and activation being then repeated at least one time and the activation of the last cycle being followed by a thermal treatment in an oxidizing atmosphere.

18 Claims, No Drawings

SUPPORTED CATALYST FOR THE OXIDATION OF ACROLEIN INTO ACRYLIC ACID

The present invention relates to a supported catalyst active in the oxidation of acrolein into acrylic acid, and a process for preparing the same. The invention also relates to the oxidation of acrolein into acrylic acid in the presence of this catalyst.

Acrylic acid is a valued intermediate having many applications in the industry, and is usually prepared by catalytic oxidation of acrolein in the vapor phase. Catalysts particularly suitable for this reaction are those which comprise mixed oxides of molybdenum, vanadium and/or tungsten, and possibly other metal oxides. The preparation of these catalysts generally comprises the impregnation of a support with an aqueous solution of decomposable salts of the metals, followed by an activation at high temperature of the thus impregnated support.

As is known, the behaviour of the catalysts in general in the process in which they are used, and that of the metal oxide catalysts in particular, depends on their chemical composition and their structural characteristics, the latter depending in turn on the process selected for the preparation of said catalysts.

An object of the present invention is to improve the conversion and selectivity values of acrylic acid produced from acrolein on a supported catalyst, by imparting a particular structure to the catalytically active part of said catalyst.

More particularly, the catalyst of the present invention comprises a silica or alumina support, and from 15 to 80% by weight, with respect to the catalyst, of a catalytically active part having the following chemical composition:

$$Mo_a V_b W_c Cu_d X_x O_y$$

wherein X is: Cr, Mn, Fe, Co, Ni, Zn, Cd, Al or Sb and wherein for a=12, b ranges from 4 to 8, c ranges from 1 to 4, d ranges from 2 to 5, x ranges from 0 to 1 and y ranges from about 17 to about 72; said active part having, moreover, an amorphous and bidimensional structure with an interplanar distance of 3.98 Å, as measured by X rays, and an IR spectrum with a somewhat broad band at 860 cm$^{-1}$ attributable to the tetrahedral coordination of the oxygen atoms with respect to the metal atoms; said catalyst being moreover obtained by impregnating the support with an aqueous solution of decomposable salts of the metals, followed by a drying of the support thus impregnated and an activation at high temperature, this operation being carried out firstly in an oxidizing atmosphere and then in an inert atmosphere, the cycle of impregnation, drying and activation being then repeated at least one time, and the catalyst being finally submitted to a thermal treatment in an oxidizing atmosphere.

It should be noted that the repetition of the treatment cycle is a critical parameter of the preparation of the catalyst according to the present invention. In fact, it has been ascertained that, by using a single cycle of impregnation, drying and activation, the active part of the catalysts thus obtained presents at X ray analysis crystalline bands due to structures different from that which is desired, the activity of these catalysts in the oxidation of acrolein into acrylic acid being insufficient or even nil in some cases.

The supports used for the catalysts of the present invention are silica and alumina. Alumina is preferably in the alpha crystallographic form, with a specific surface area lower than 1 m$^2$/g and with pore diameters of from 20 to 180 microns.

This alpha-alumina, in the form of spheres of from 4 to 8 mm in size, is useful in the case of the use of the catalyst in the form of a fixed bed, and in this case the catalyst advantageously contains from 15 to 40% by weight of active part, values of the order of 18-20% by weight being preferred. The silica is preferably a commercial microspheroidal silica with a specific surface area of the order of 600 m$^2$/g and an average pore diameter of 60-80 Å. This silica in the form of particles of from 40 to 150 microns may be used in the case of a fluidized catalyst, and in this case the catalyst may contain from 15 to 80% by weight of active part, values of the order of 30-40% by weight being preferred.

In each case the active part is applied on the support by using at least two cycles which comprise each an impregnation of the support, a drying of the impregnated support and an activation at high temperature. In each of these cycles a fraction of the active part is applied on the support, to reach the desired overall value at the last cycle.

The impregnation may be carried out by using an aqueous solution of decomposable salts of the metals. Examples of suitable salts are ammonium paramolybdate, ammonium metavanadate, ammonium tungstate, copper, zinc and iron nitrates, copper acetate and iron oxalate. The aqueous solutions used for the impregnation may conveniently contain about 20-40% by weight of decomposable salts, even if more dilute solutions may be used.

Although the impregnating solution used for a cycle of operations may be brought into contact with the support in a single step, it is preferable to carry out a series of impregnation steps with portions of said impregnating solution, each impregnation step being followed by a drying. The impregnation, or each individual impregnation step, may be carried out at ambient temperature. However, it is preferable to operate at higher temperatures, such as temperatures of from 40° C. up to the temperature of incipient boiling of the solution used. The apparatus used for the impregnation may be chosen from those in which the solid particles can be kept under motion, thus to allow a good homogenization between support and impregnating solution, such as for example rotating drums. Obviously, the quantity of impregnating solution used in one or more impregnations may vary in dependence on the quantity of catalytically active part which it is desired to apply on the support during the corresponding cycle of operations. Moreover, the ratio between the individual salts in the impregnating solution is chosen as a function of the desired chemical composition, within the ranges indicated above. In each case, after the impregnation, or after each individual impregnation step, a drying of the impregnated support is carried out at a temperature of the order of 100°-130° C., preferably in a stream of air.

As previously stated, the activation is carried out at elevated temperature, firstly in an oxidizing atmosphere and then in an inert atmosphere. More particularly, the activation may be carried out according to the following general method:

step (a): gradual increase in the temperature from the values used for the drying up to values of the order of 220°-250° C., and period of stay at these last values, the whole being carried out in the presence of air;

step (b): replacement of air by nitrogen, rise in temperature up to values of the order of 380°-400° C., and period of stay at these last temperatures until the evolution of gases such as ammonia deriving from the decomposition of the salts is substantially completed.

According to a preferred embodiment:

in step (a) the temperature is gradually brought from the drying values up to 230°-240° C., using a heating gradient of about 5° C. per 30 minutes, and the temperature is then kept at 230°-240° C. for 10-15 hours, the whole being carried out in the presence of air;

in step (b) air is replaced by nitrogen, the temperature is then brought to 380°-400° C. in a period of 3-8 hours, and the temperature is kept at these last values until completion of the ammonia evolution. Conveniently, a gaseous pressure of about 1 kg/cm$^2$ is applied, the gaseous atmosphere being gradually removed by means of a slight nitrogen steam.

According to the present invention, the cycle of operations described above is repeated at least one time, to confer on the catalyst, or better on its active part, those planar arrangement and bidimensional structure which make it active and selective in the oxidation of acrolein into acrylic acid. Although the number of cycles may be very high, it is found in practice that two or three cycles of impregnation, drying and activation are sufficient to confer on the catalyst the desired characteristics. At the end of the last cycle, the catalyst is heated in air at elevated temperature, and preferably at a temperature of the order of 380°-400° C. According to a preferred embodiment, ammonia and the other gases evolved during the last activation operation are removed by means of a nitrogen stream, the nitrogen is then replaced by air, and the temperature is kept at 380°-400° C. for a further 4-8 hours. At the end of this period of time, the catalyst is cooled and recovered.

The catalysts according to the present invention may be used in the form of a fixed bed when the support is alumina, and in the form a fluidized bed when the support is silica.

In particular, acrylic acid is produced by flowing through the catalyst a gaseous stream containing from 1 to 8% in volume of acrolein, and from 0.5 to 20% in volume of oxygen, the remaining percentage consisting of inert gases such as nitrogen, carbon dioxide and steam. Moreover, it is convenient to maintain in the feed a molar ratio between acrolein and oxygen of from 0.1:1 to 4:1, and preferably from 0.2:1 to 2:1. The reaction is carried out at a temperature of from 220° to 350° C. (preferably from 250° to 320° C.), without applying any overpressure, or else by applying a slight overpressure, up to 2-3 kg/cm$^2$.

The contact times are generally from 1 to 10 seconds, and in the case of a fluidized bed the gas velocity is maintained at a value of from 5 to 50 cm/second to achieve a good fluidization of the catalyst.

By operating under these conditions, high conversions of acrolein and high selectivities for acrylic acid are obtained, as will be shown in the following experimental examples. Moreover, the mechanical characteristics of the catalyst of the present invention are such as to permit its use for industrially useful periods of time.

EXAMPLE 1

There is used a support consisting of alpha-alumina with a specific surface area lower than 1 m$^2$/g and an overall pore volume of 0.19 ml/g. The pore diameter of the alumina is from 20 to 180 microns and its grain size is from 6 to 8 mm.

The two following aqueous solutions are prepared:

solution A:

for each liter of water, the solution comprises 8.92 g of ammonium dichromate $(NH_4)_2Cr_2O_7$, 250.12 g of ammonium paramolybdate $(NH_4)_6Mo_7O_{24}.4H_2O$, 63.52 g of ammonium metavanadate $NH_4VO_3$ and 73.96 g of ammonium tungstate $5(NH_4)0.12WO_3.5H_2O$.

solution B:

for each liter of water the solution contains 62.754 g of copper nitrate $Cu(NO_3)_2.3H_2O$.

A series of nine impregnations and nine subsequent dryings is carried out, by combining 5.3 parts by weight of solution A with one part by weight of solution B, and using for each impregnation a quantity of combined solutions corresponding to 1.6-1.7% by weight of active part in the final catalyst. More particularly, the portion of solution A is heated to 55°-60° C., as well as the corresponding portion of solution B, the two portions are combined, and the resulting solution is poured on the alumina (1460 g) heated to 55°-60° C. and maintained in motion in a rotating drum. At the end of each impregnation step, the impregnated support is dried in an oven at 120° C. for 12 hours, under a stream of air. After the last drying, the temperature is brought from 120° to 235° C. gradually in 11 hours, and is maintained at 235° C. for a further 12 hours, still in the presence of air. The air is then replaced by nitrogen and the temperature is brought to 400° C. in 5.5 hours. The temperature is maintained at 400° C. for two hours, the ammonia evolved being removed by means of a slight nitrogen flow and the atmosphere being maintained at about 1 kg/cm$^2$. At the end of this period of time, the mass is cooled and there is obtained a green-black catalyst of fragile appearance containing 15% by weight of active part.

Using the same operative conditions, four further impregnations and dryings are carried out. The catalyst is then activated in the manner indicated above, and at the end of the treatment in a nitrogen atmosphere, the mass is kept at 400°-410° C. for 4 hours in an air atmosphere. The mass is then cooled and the catalyst thus obtained contains 18.5-19% by weight of active part, the remaining percentage consisting of the support.

The said active part contains the metallic components Mo:V:W:Cu:Cr in the following atomic ratios 12:4.6:2.4:2.2:0.6. Moreover, X ray analysis of the catalytically active part shows a bidimensional and completely amorphous structure with an interplanar distance of 3.98 Å, and the IR spectrum presents a broadened band at 860 cm$^{-1}$ attributable to the tetrahedral coordination of the oxygen atoms with respect to the metal atoms.

The catalyst is black and compact, the active part being adhesively linked to the support.

EXAMPLE 2

The catalyst of Example 1 is used for the oxidation of acrolein into acrylic acid.

A tubular reactor with an internal diameter of 12 mm is loaded with 105 ml of catalyst (degree of filling of about 62%) and then placed in a bath of fused salts at a temperature of 308° C. The volume of the fixed catalytic bed is 169 ml. The reactor is fed with a gaseous stream having the following volumetric composition:

| | |
|---|---|
| oxygen | 4.94% |
| nitrogen | 60.09% |
| acrolein | 4.13% |
| water | 30.84%. |

The reaction is carried out without applying any overpressure, with a linear gas velocity of 111 cm/second, with a contact time of 1.26 seconds and with a space velocity of 1384 h$^{-1}$.

Analysis of the gaseous stream issuing from the reactor shows the following volumetric composition:

| | |
|---|---|
| oxygen | 3.12% |
| nitrogen | 60.44% |
| acrolein | 0.83% |
| water | 32.14% |
| acrylic acid | 3.2% |
| acetic acid | 0.062% |
| carbon monoxide | 0.03% |
| carbon dioxide | 0.169%. |

The acrolein conversion is thus 80% with a selectivity for acrylic acid of 97%. The output in acrylic acid is 150 g per liter of catalyst and per hour.

EXAMPLE 3

The catalyst of Example 1 is used under the conditions of Example 2 in a reactor having a diameter of about 5 cm. The degree of filling of this reactor is proportionally increased with respect to that of Example 2. By degree of filling is meant the volume actually occupied by the catalyst granules with respect to the useful volume of the empty reactor. In this case the methanol conversions were 97-98% with a selectivity for acrolein of 96%.

EXAMPLE 4

The support is a microspheroidal silica with a surface area of about 600 m$^2$/g and an overall pore volume of about 1 ml/g. The average pore diameter of this silica is 65 Å and the grain size is from 40 to 80 microns.

The following aqueous solutions are prepared:
solution A:
in 8 liters of water heated at 98° C. there are dissolved 452 g of ammonium metavanadate NH$_4$VO$_3$, 168 g of ammonium tungstate 5(NH$_4$)0.12WO$_3$. 5H$_2$O and 1250 g of ammonium paramolybdate (NH$_4$)$_6$Mo$_7$O$_{24}$.4H$_2$O.
solution B:
in one liter of water there are dissolved 622 g of copper nitrate Cu(NO$_3$)$_2$.3H$_2$O.

3.5 kg of commercial silica G 951, corresponding to 3.25 liters, are used. This silica is submitted to two impregnations, followed each by a drying at 120° C.

More particularly, the solution used in the two impregnation steps are as follows:

1st impregnation: 2.9 liters of solution A +0.25 liters of solution B.

2nd impregnation: 2.7 liters of solution A +0.25 liters of solution B.

After the second drying, the temperature is brought in 11 hours from 120° to 235° C. and is maintained at this last value for the following 12 hours, in the presence of air. The air is then replaced by nitrogen and the temperature is brought to 380° C. in 5 hours, and then maintained at 380°-400° C. for 2 hours, the ammonia evolved being removed and the atmosphere being maintained at a pressure of about 1 kg/cm$^2$. After this period of time, the residual ammonia is removed by circulating for a short time a light nitrogen stream, and the mass is cooled. Two further impregnations are then carried out as follows:

3rd impregnation: 2.2 liters of solution A +0.25 liters of solution B,

4th impregnation: 2.0 liters of solution A +0.25 liters of solution B.

After each impregnation the mass is dried as indicated above; and after the last drying, the cycle of thermal treatments described above is repeated. At the end of the cycle, the mass is kept at 400° C. for four hours in an atmosphere of air. The mass is then cooled, and the catalyst thus obtained contains 33% by weight of active part, in which the metallic components Mo:V:W:Cu are present in the following atomic ratios: 12:6.5:1.1:4.3.

The X ray analysis and IR spectrum show the structural characteristics described in connection with the catalyst of Example 1.

EXAMPLE 5

The catalyst of Example 4 is used for the oxidation of acrolein into acrylic acid, in a fluid-bed reactor consisting of a steel tube with a diameter of 6.1 cm, a height of 96 cm and a capacity of 2 liters, provided with an expansion chamber of 12 cm in diameter and 40 cm in height. 9 foraminous plates having each 60 holes of 3 mm, are arranged in the reactor at a distance of 60 mm from each other.

2 liters of catalyst are loaded into the reactor, and a gaseous flow having the following volumetric composition is passed through the fluidized bed:

| | |
|---|---|
| oxygen | 7.89 |
| nitrogen | 53.53% |
| acrolein | 5.08% |
| water | 33.50% |

The reaction is carried out without applying any overpressure, with a linear gas velocity of 20 cm/sec., with a contact time of 4.68 seconds and with a space velocity of 392 h$^{-1}$. The volumetric composition of the gaseous stream discharged from the reactor is as follows:

| | |
|---|---|
| oxygen | 1.99% |
| nitrogen | 57.77% |
| acrolein | 0.33% |
| water | 34.70% |
| acrylic acid | 4.43% |
| acetic acid | 0.18% |
| carbon monoxide | 0.18% |
| carbon dioxide | 0.42%. |

The acrolein conversion is thus 93.4% with a selectivity for acrylic acid of 93.6%. The output is 55.6 g of acrylic acid per liter of catalyst and per hour.

EXAMPLE 6

The test of Example 5 is repeated, using the catalyst of Example 4 and heating the fluidized bed at 255° C. The gaseous mixture delivered to the fluidized bed has the following volumetric composition:

| | |
|---|---|
| oxygen | 7.43% |
| nitrogen | 54.10% |
| acrolein | 5.22% |

| | |
|---|---|
| water | 33.25% |

The reaction is carried out at atmospheric pressure, with a linear gas velocity of 20.08 cm/second, with a contact time of 4.7 seconds and with a space velocity of 393 h$^{-1}$. Under these conditions the gaseous stream issuing from the reactor has the following volumetric composition:

| | |
|---|---|
| oxygen | 1.16% |
| nitrogen | 57.89% |
| acrolein | 0.20% |
| water | 35.06% |
| acrylic acid | 4.59% |
| acetic acid | 0.20% |
| carbon monoxide | 0.22% |
| carbon dioxide | 0.68% |

The acrolein conversion is thus 96.15% with a selectivity for acrylic acid of 92%. The output of acrylic acid is 57.84 g per liter of catalyst and per hour.

We claim:

1. A catalyst active in the oxidation of acrolein into acrylic acid, which comprises a silica or alumina support and from 15 to 80% by weight, with respect to the catalyst, of a catalytically active part having the following chemical composition

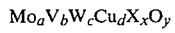

$$Mo_aV_bW_cCu_dX_xO_y$$

wherein X is Cr, Mn, Fe, Co, Ni, Zn, Cd, Al or Sb and wherein for a=12, b ranges from 4 to 8, c ranges from 1 to 4, d ranges from 2 to 5, x ranges from 0 to 1 and y ranges from about 17 to about 72; said active part having an amorphous and bidimensional structure with an interplanar distance of 3.98 Å, as measured by X rays; and an IR spectrum with a somewhat broad band at 860 cm$^{-1}$ attributable to the tetrahedral coordination of the oxygen atoms with respect to the metal atoms; and said catalyst being obtained by impregnating the support with an aqueous solution of decomposable salts of the metals of said active part, drying the thus impregnated support and activating at high temperature the support thus dried, the activation stage being carried out firstly in an oxidizing atmosphere and then in an inert atmosphere, the cycle of impregnation, drying and activation being then repeated at least one time and the activation of the last cycle being followed by a thermal treatment in an oxidizing atmosphere.

2. The catalyst of claim 1, wherein the support is an alpha-alumina with a surface area of less than 1 m$^2$/g and a pore diameter of from 20 to 180 microns, in the form of spheres with a size of from 4 to 8 mm, said catalyst containing from 15 to 40% by weight of said active part.

3. The catalyst of claim 1, wherein the support is a microspheroidal silica with a surface area of the order of 600 m$^2$/g and a pore diameter of from 60 to 80 Å, in the form of particles with a size of from 40 to 150 microns.

4. The catalyst of claim 3, which comprises from 30 to 40% by weight of said active part.

5. The catalyst of claim 1, characterized in that the impregnation is carried out at a temperature of from ambient temperature up to the temperature of incipient boiling of the said aqueous solution.

6. The catalyst of claim 1, characterized in that the impregnation is carried out at a temperature of from 40° C. to the temperature of incipient boiling of the said aqueous solution.

7. The catalyst of claim 1, characterized in that the impregnation stage is carried out by using two or more impregnation steps, followed each by a drying.

8. The catalyst of claim 1, characterized in that the drying is carried out at a temperature of about 100°–130° C.

9. The catalyst of claim 1, characterized in that the drying is carried out in a stream of air.

10. The catalyst of claim 1, characterized in that the activation is carried out by bringing the temperature from the drying temperature up to 220°–250° C., maintaining the temperature at 220°–250° C. in an atmosphere of air, replacing the air by nitrogen, bringing the temperature to 380°–400° C. and maintaining the temperature at 380°–400° C. still in an atmosphere of nitrogen until the evolution of gaseous substances deriving from the decomposition of the salts is substantially completed.

11. The catalyst of claim 1, characterized in that the activation is carried out by bringing the temperature from the drying temperature up to 230°–240° C. using a heating gradient of about 5° C. per 30 minutes, maintaining the temperature at 230°–240° C. for about 10–15 hours in an atmosphere of air, replacing the air by nitrogen, bringing the temperature to 380°–400° C. in a period of about 3–8 hours and maintaining the temperature at 380°–400° C. still in an atmosphere of nitrogen and under a gaseous pressure of about 1 Kg/cm$^2$, until the evolution of gaseous substances deriving from the decomposable salts is substantially completed.

12. The catalyst of claim 1, characterized in that the thermal treatment is carried out at 380°–400° C. for about 4–8 hours in the presence of air.

13. The catalyst of claim 8, characterized in that the activation stage being carried out at a temperature of about 220°–400° C.

14. The catalyst of claim 8, characterized in that the activation is carried out by bringing the temperature from the drying temperature up to 220°–250° C., maintaining the temperature at 220°–250° C. in an atmosphere of air, replacing the air by nitrogen, bringing the temperature to 380°–400° C. and maintaining the temperature at 380°–400° C. still in an atmosphere of nitrogen until the evolution of gaseous substances deriving from the decomposition of the salts is substantially completed.

15. The catalyst of claim 8, characterized in that the activation is carried out by bringing the temperature from the drying temperature up to 230°–240° C. using a heating gradient of about 5° C. per 30 minutes, maintaining the temperature at 230°–240° C. for about 10–15 hours in an atmosphere of air, replacing the air by nitrogen, bringing the temperature to 380°–400° C. in a period of about 3–8 hours and maintaining the temperature at 380°–400° C. still in an atmosphere of nitrogen and under a gaseous pressure of about 1 Kg/cm$^2$, until the evolution of gaseous substances deriving from the decomposable salts is substantially completed.

16. The catalyst of claim 1, wherein said catalyst has been obtained by a process consisting essentially of said impregnating, said drying, said activating and said thermal treatment.

17. The catalyst of claim 1, wherein said catalyst has been obtained by a process consisting of said impregnating, said drying, said activiating, with the cycle of impregnation, drying and activation being then repeated at least one time, and said thermal treatment after the completion of the last cycle of activation.

18. A catalyst active in the oxidation of acrolein into acrylic acid, which comprises a silica or alumina support and from 15 to 80% by weight, with respect to the catalyst, of a catalytically active part having the following chemical composition $$Mo_a V_b W_c Cu_d X_x O_y$$

wherein X is Cr, Mn, Fe, Co, Ni, Zn, Cd, Al or Sb and wherein for a=12, b ranges from 4 to 8, c ranges from 1 to 4, d ranges from 2 to 5, x ranges from 0 to 1 and y ranges from about 17 to about 72; said active part having an amorphous and bidimensional structure with an interplanar distance of 3.98 Å, as measured by X rays; and an IR spectrum with a somewhat broad band at 860 $cm^{-1}$ attributable to the tetrahedral coordination of the oxygen atoms with respect to the metal atoms.

* * * * *